United States Patent
Liu et al.

(10) Patent No.: US 10,460,480 B2
(45) Date of Patent: Oct. 29, 2019

(54) RECONSTRUCTING PET IMAGE

(71) Applicant: Shenyang Neusoft Medical Systems Co., Ltd., Shenyang (CN)

(72) Inventors: Yue Liu, Shenyang (CN); Zhipeng Sun, Shenyang (CN); Ming Li, Shenyang (CN)

(73) Assignee: Shenyang Neusoft Medical Systems Co., Ltd., Shenyang, Liaoning (CN)

(*) Notice: Subject to any disclaimer, the term of this patent is extended or adjusted under 35 U.S.C. 154(b) by 219 days.

(21) Appl. No.: 15/819,334

(22) Filed: Nov. 21, 2017

(65) Prior Publication Data
US 2018/0144513 A1 May 24, 2018

(30) Foreign Application Priority Data

Nov. 24, 2016 (CN) .......................... 2016 1 1058788

(51) Int. Cl.
*G06T 11/00* (2006.01)
*A61B 6/03* (2006.01)
(Continued)

(52) U.S. Cl.
CPC ............ *G06T 11/005* (2013.01); *A61B 6/037* (2013.01); *A61B 6/5205* (2013.01);
(Continued)

(58) Field of Classification Search
CPC ......... G06T 11/003–006; G06T 7/0012; G06T 2207/10104; G06T 1/2985; G06T 1/1648;
(Continued)

(56) References Cited

U.S. PATENT DOCUMENTS 7,039,227 B2 *  5/2006  Tanaka .................. G01T 1/2985
                                                    250/363.03
7,129,496 B2 * 10/2006  Stearns ................. G01T 1/2985
                                                    250/363.03
(Continued)

OTHER PUBLICATIONS

"Deep reconstruction model for dynamic PET images", Jianan Cui, PLoS ONE. Sep. 21, 2017, vol. 12 Issue 9, p. 1-21. 21p. (Year: 2017).*

(Continued)

*Primary Examiner* — Michael S Osinski
(74) *Attorney, Agent, or Firm* — Fish & Richardson P.C.

(57) ABSTRACT

Methods, devices, and systems for reconstructing Positron Emission Computed Tomography (PET) images are provided. In one aspect, a method includes: for each of coincidence events including at least one true coincidence event and at least one scattering coincidence event, determining an emission path of the coincidence event according to photon information of the coincidence event, the photon information of the coincidence event including time data, position data, and angle data of each of two photons involved in the coincidence event, determining an annihilation position of the coincidence event according to the emission path of the coincidence event and the time data of each of the two photons involved in the coincidence event, and reconstructing a PET image according to the annihilation position, the emission path and the photon information of each of the coincidence events.

20 Claims, 6 Drawing Sheets

(51) Int. Cl.
*G06T 7/00* (2017.01)
*A61B 6/00* (2006.01)

(52) U.S. Cl.
CPC .......... *A61B 6/5282* (2013.01); *G06T 7/0012* (2013.01); *G06T 11/006* (2013.01); *G06T 2207/10104* (2013.01)

(58) Field of Classification Search
CPC ....... G06T 1/1615; G06T 1/172; G06T 1/249; A61B 6/5205; A61B 6/5282; A61B 6/5258; A61B 6/5235; A61B 6/037; A61B 6/032; G01R 33/481
See application file for complete search history.

(56) References Cited

U.S. PATENT DOCUMENTS

| | | | | |
|---|---|---|---|---|
| 7,312,455 | B2* | 12/2007 | Manjeshwar | G01T 1/2985 |
| | | | | 250/363.03 |
| 7,381,959 | B2* | 6/2008 | Manjeshwar | G01T 1/2985 |
| | | | | 250/363.03 |
| 7,381,960 | B1* | 6/2008 | Chuang | G01T 1/1603 |
| | | | | 250/363.03 |
| 7,970,214 | B2* | 6/2011 | Kadrmas | G06T 11/003 |
| | | | | 382/232 |
| 8,094,908 | B2* | 1/2012 | Stearns | A61B 6/037 |
| | | | | 250/363.04 |
| 8,183,531 | B2* | 5/2012 | Chinn | G01T 1/2985 |
| | | | | 250/252.1 |
| 8,384,036 | B2* | 2/2013 | Conti | G01T 1/2985 |
| | | | | 250/363.03 |
| 8,575,554 | B2* | 11/2013 | Qian | G01T 1/1615 |
| | | | | 250/363.03 |
| 8,767,908 | B2* | 7/2014 | Leahy | G01T 1/2985 |
| | | | | 250/363.04 |
| 8,923,588 | B2* | 12/2014 | Laurence | G01T 1/2985 |
| | | | | 382/131 |
| 8,987,659 | B2* | 3/2015 | Laurence | G01T 1/1648 |
| | | | | 250/252.1 |
| 9,291,725 | B2* | 3/2016 | Wang | G01T 1/2985 |
| 9,962,136 | B2* | 5/2018 | Pratx | A61B 6/037 |
| 10,034,640 | B2* | 7/2018 | Douglas | G01T 1/2985 |
| 10,101,474 | B2* | 10/2018 | Laurence | G01T 1/171 |
| 10,147,206 | B2* | 12/2018 | Li | G06T 11/003 |
| 10,215,864 | B2* | 2/2019 | Herraiz | G01T 1/1647 |
| 10,319,118 | B2* | 6/2019 | Sun | G01S 7/4866 |
| 2006/0266946 | A1* | 11/2006 | Defrise | G01T 1/2985 |
| | | | | 250/363.03 |
| 2007/0106154 | A1* | 5/2007 | Conti | G01T 1/1611 |
| | | | | 600/436 |
| 2009/0309031 | A1* | 12/2009 | Ohtani | G01T 1/2985 |
| | | | | 250/363.03 |
| 2013/0009064 | A1* | 1/2013 | Yoshida | G01T 1/2985 |
| | | | | 250/362 |
| 2015/0289825 | A1* | 10/2015 | Lage | G06T 11/005 |
| | | | | 600/425 |
| 2016/0131774 | A1* | 5/2016 | Lage | A61B 6/481 |
| | | | | 600/426 |
| 2017/0082759 | A1* | 3/2017 | Lyu | G01T 1/2985 |
| 2017/0164911 | A1* | 6/2017 | Lv | A61B 6/037 |
| 2017/0332983 | A1* | 11/2017 | Tai | G01T 1/2985 |
| 2018/0116621 | A1* | 5/2018 | Berker | A61B 5/0035 |
| 2019/0018154 | A1* | 1/2019 | Olcott | G01T 1/208 |
| 2019/0066342 | A1* | 2/2019 | Zhu | G06T 11/005 |

OTHER PUBLICATIONS

"Focus on time-of-flight PET: the benefits of improved time resolution", Maurizio Conti, European journal of nuclear medicine and molecular imaging, 2011 (Year: 2011).*
"Update on Time-of-Flight PET Imaging", Suleman Surti, Journal of Nuclear Medicine, 2015 (Year: 2015).*
"Image reconstruction for PET/CT scanners: past achievements and future challenges", Shan Tong, Imaging Med. Oct. 1, 2010; 2(5): 529-545. (Year: 2010).*

* cited by examiner

RECONSTRUCTING PET IMAGE

CROSS REFERENCE TO RELATED APPLICATIONS

This application claims priority to Chinese Patent Application No. 201611058788.7, filed on Nov. 24, 2016, the entire content of which is incorporated herein by reference.

TECHNICAL FIELD

The present disclosure relates to methods, devices, and systems for reconstructing a Positron Emission Computed Tomography (PET) image.

BACKGROUND

Positron Emission Computed Tomography (PET) technology has been widely applied to biomedical research fields such as tumor early detection, drug screening and the like. By injecting a radioactive tracer into a subject's body and detecting photons produced by an annihilation event outside the subject's body with a PET device, the PET technology may be used to obtain spatial distribution of the tracer inside the subject's body according to data collected by the PET device, thereby indirectly obtaining physiological metabolism information of the subject. A γ-photon produced by an annihilation event may be detected by a crystal of a PET device, and data collected by the PET device may include true coincidence data, scattering coincidence data and random coincidence data. When reconstructing a PET image with the collected data, the scattering coincidence data and the random coincidence data may be removed from the collected data. For example, the scattering coincidence data may be removed according to a scattering correction factor and the random coincidence data may be removed according to a random correction factor. However, since the scattering coincidence data is derived from two photons which are produced by one annihilation event and one of the two photons deflects in angle, directly removing the scattering coincidence data may lead to loss of a part of the collected data. In this way, the collected coincidence data may not be fully utilized. Further, the process of removing scattering coincidence data may increase the amount of calculation and reduce the efficiency of image reconstruction.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

The present disclosure provides methods, systems, and machine-readable storage mediums for reconstructing a PET image by obtaining an emission path of a scattering coincidence event and applying the scattering coincidence data to the reconstruction of the PET image, which can save time for correcting the scattering coincidence data with scattering correction and fully utilize collected data to improve PET sensitivity and an image quality of the reconstructed PET image.

One innovative aspect of the subject matter described in the present disclosure can be embodied in methods that include the actions of, for each of coincidence events comprising at least one true coincidence event and at least one scattering coincidence event, determining an emission path of the coincidence event according to photon information of the coincidence event, the photon information of the coincidence event including time data, position data, and angle data of each of two photons involved in the coincidence event; determining an annihilation position of the coincidence event according to the emission path of the coincidence event and the time data of each of the two photons involved in the coincidence event; and reconstructing the PET image according to the annihilation position, the emission path and the photon information of each of the coincidence events.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination. For example, determining the emission path of the coincidence event can include: for each of the two photons involved in the coincidence event, obtaining a respective emission path according to the position data and the angle data of the photon; and determining an intersecting point of the respective emission paths of the two photons to obtain the emission path of the coincidence event. The method can further include: for each of the photons involved in the coincidence event, obtaining respective incidence intersecting positions on at least two crystal layers of a crystal array, the incidence intersecting positions indicating a travelling trace of the photon incident into the crystal array; and obtaining the angle data of the photon incident into the crystal array according to the respective incidence intersecting positions. The position data of the photon can include an incidence intersecting position of the photon on a crystal layer at which the photon arrives finally in the crystal array.

In some implementations, determining the annihilation position of the coincidence event includes: obtaining a difference of traveling time of the two photons before detected according to the time data of each of the two photons involved in the coincidence event; determining a difference of traveling distance of the two photons along the emission path according to a velocity of light and the traveling time difference; and determining the annihilation position in the emission path according to the traveling distance difference and the emission path.

The method can further include: performing a random correction to remove a random coincidence event from the coincidence events before determining the respective emission paths of the coincidence events.

In some cases, performing the random correction includes: delaying a respective single event in each of the coincidence events by a period of time to obtain delayed coincidence data, a length of the period of time being larger than a coincidence time window; and removing the delayed coincidence data from coincidence data of the coincidence events.

In some cases, performing the random correction includes: for each of the coincidence events, obtaining a Line of Response associated with the determined emission path; obtaining respective single photon counting rates of two crystals associated with the Line of Response; determining random coincidence data for the Line of Response according to the single photon counting rates of the two crystals and a coincidence time window; and removing the random coincidence data for the Line of Response from coincidence data of the coincidence events.

In some implementations, reconstructing the PET image according to the annihilation position, the emission path and the photon information of each of the coincidence events includes: determining one or more model parameters of an image reconstruction model according to the annihilation position, the emission path and the photon information of each of the coincidence events; constructing the image reconstruction model according to the model parameters; deriving an iterative reconstruction formula from the image reconstruction model; and reconstructing the PET image with the iterative reconstruction formula.

The image reconstruction model can be expressed as:

$Y_j = P_{ij} X_i A_j N_j + R_j$, where j represents an emission path of the coincidence event, $Y_j$ represents coincidence data of the coincidence event on the emission path j, $X_i$ represents an i-th voxel in the PET image, $P_{ij}$ represents a probability that the i-th voxel is received by the emission path j, $A_j$ represents an attenuation probability on the emission path j, $N_j$ represents a normalization factor on the emission path j, and $R_j$ represents random coincidence data on the emission path j.

Determining the one or more model parameters of the image reconstruction model can include: obtaining j from the determined emission paths of the coincident events, determining $A_j$ and $N_j$ based on the emission path j, determining $X_i$ based on the annihilation position, and determining $P_{ij}$ based on the angle data and the time data of two crystals involved in the i-th voxel and the emission path j.

The details of one or more examples of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

Coincidence events collected by a PET device may include: a true coincidence event, a scattering coincidence event, and a random coincidence event.

Figure 1A:
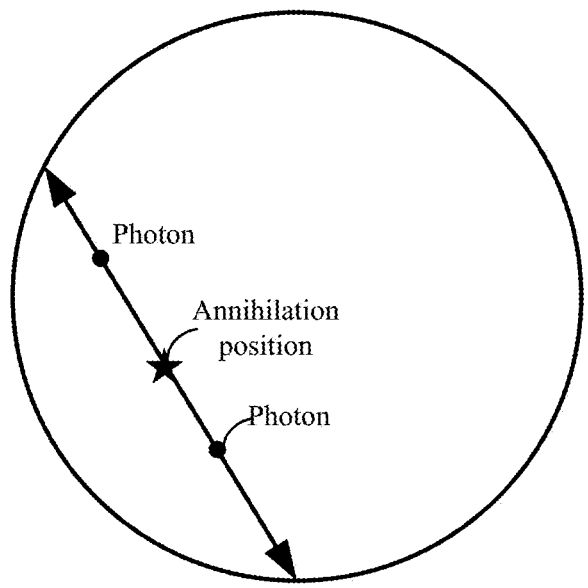
FIG. 1A is a schematic diagram of a true coincidence event according to an example of the present disclosure.

A true coincidence event may include, for example, two photons produced by one annihilation event. As shown in FIG. 1A, the two photons may be emitted in opposite directions which are approximately 180 degrees.

Figure 1B:
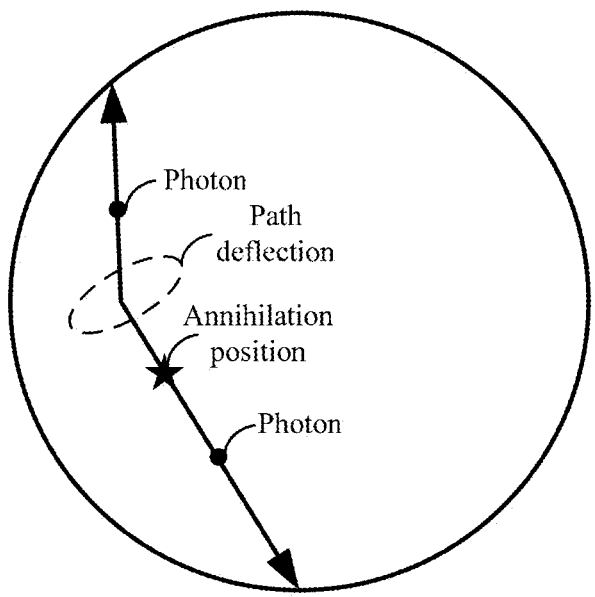
FIG. 1B is a schematic diagram of a scattering coincidence event according to an example of the present disclosure.

A scattering coincidence event may include, for example, two photons produced by one annihilation event. As shown in FIG. 1B, one of the two photons may deflect from its original direction during emission, which can form an emission direction of a folding line. The scattering coincidence event may further include a case where the two photons both deflect from their original directions during emission. However, this case may happen with extremely low probability and therefore this case is not considered in the present disclosure.

A random coincidence event may include, for example, two photons produced by two annihilation events.

Data concerning a coincidence event may be referred to as coincidence data. For example, data concerning a true coincidence event may be referred to as true coincidence data. Since the scattering coincidence data is also derived from two photons produced by one annihilation event, when reconstructing a PET image, if correct emission paths of two photons involved in a scattering coincidence event are obtained, the scattering coincidence data may also be applied to the reconstruction of the PET image. In this way, time for correcting the scattering coincidence data with a scattering correction factor may be saved and the collected data may be fully utilized to improve the sensitivity of the PET device.

In the present disclosure, the PET image may be reconstructed based on Time-of-Flight PET (TOF-PET). Before the PET image is reconstructed, an emission path for an annihilation event, such as, a Line of Response (LOR) and an annihilation position of the annihilation event in the emission path can be obtained first.

A method of reconstructing a PET image in the present disclosure will be described in detail as follows.

Taking a double coincidence event (only two single events are included within a predetermined coincidence time window τ) for example, one double coincidence event (hereinafter, may be referred to as coincidence event) may involve two photons, and photon information of the coincidence event may be stored and recorded in a list mode. For example, the following Table 1 illustrates the photon information of two coincidence events recorded in the list mode.

TABLE 1

The photon information of two coincidence events

| | First Photon | | | Second Photon | | |
|---|---|---|---|---|---|---|
| | Time | Position | Angle | Time | Position | Angle |
| Coincidence event A | data a1 | data a1 | data a1 | data a2 | data a2 | data a2 |
| Coincidence event B | data b1 | data b1 | data b1 | data b2 | data b2 | data b2 |

As shown in above Table 1, each coincidence event may involve two photons, and the photon information of the coincidence event may include time data, position data and angle data. Where, time data may be used to indicate a time at which the photon is received by a crystal; position data may be used to indicate a position of the crystal which receives the photon; and angle data may be used to indicate an angle at which the photon is incident on the crystal.

The following descriptions are directed to obtaining "position data" and "angle data" for each coincidence event.

Figure 2:
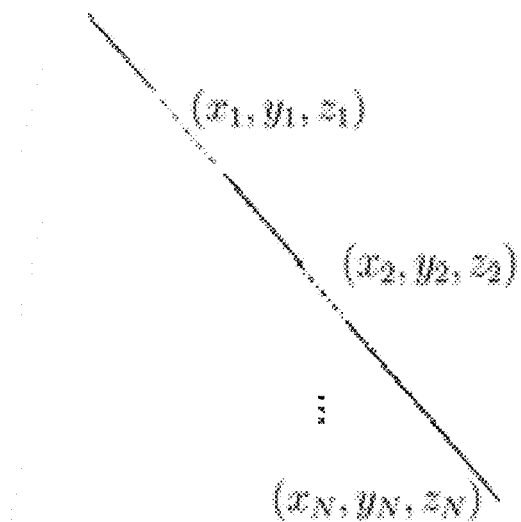
FIG. 2 is a schematic diagram of an incidence intersecting position of a photon on each crystal layer according to an example of the present disclosure.

For example, taking a position sensitive detector (e.g., any detector capable of measuring a photon incidence vector is applicable, without limitation to the position sensitive detector) for example, the detector may include a layered crystal array and record a position at which a photon hits each crystal layer. Assuming the layered crystal array has N layers in total, the position at which the photon hits each crystal layer i is $(x_i, y_i, z_i)$, i=1, 2 . . . , N when the photon is incident into the layered crystal array, and the position at which the photon hits each crystal layer i may be referred to as an incidence intersecting position. FIG. 2 illustrates a schematic diagram of an incidence intersecting position of a photon on each crystal layer. A photon may not necessarily intersect with all crystal layers, but may intersect with at least two crystal layers. Respective incidence intersecting positions on the at least two crystal layers of the layered crystal array which indicate a travelling trace of the photon incident into the crystal array may be obtained.

"Angle data" in the photon information in Table 1 may include an incidence vector $\vec{V}$ of the photon that may be obtained according to the incidence intersecting position of the photon on each crystal layer. For example, the incidence vector may be obtained by fitting and the like, and alternatively, may also be determined according to the following formula:

$$\vec{V}=(x_j-x_1, y_j-y_1, z_j-z_1) j \in \{2,3 \ldots, N\},$$

where j may be any integer from 2 to N.

"Position data" in the photon information, such as, $(x_2, y_2, z_2)$, may indicate an incidence intersecting position of the photon on a crystal layer at which the photon arrives finally. The above layered crystal array is still taken for example.

Assuming that a photon passes through a first crystal layer and a second crystal layer, and finally stops at a third crystal layer during entering into the layered crystal array, it is equivalent to that the photon is detected by a particular crystal of the third crystal layer. During entering into the layered crystal array, the photon has an incidence intersecting position on the first crystal layer, the second crystal layer and the third crystal layer, respectively, and the incidence vector can be determined according to any two incidence intersecting positions. "Position data" of the photon indicates an incidence intersecting position $(x_3, y_3, z_3)$ of the photon on the third crystal layer.

Figure 3:
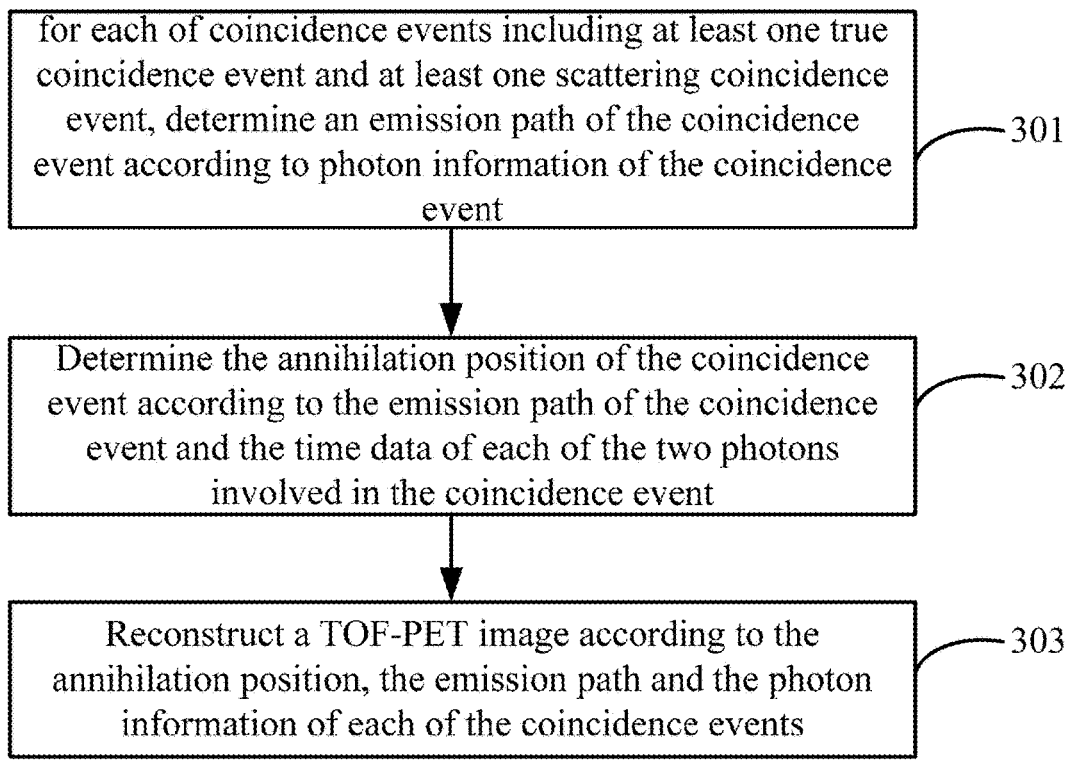
FIG. 3 is a flow diagram of a process of a method of reconstructing a PET image according to an example of the present disclosure.

A PET image can be reconstructed according to the above photon information recorded in the list mode. FIG. 3 is a flow diagram of a process of a method of reconstructing a PET image according to an example of the present disclosure. The process may include step 301 to step 303.

At step 301, for each of coincidence events including at least one true coincidence event and at least one scattering coincidence event, an emission path of the coincidence event is determined according to photon information of the coincidence event.

The photon information of the coincidence event may include time data, position data, and angle data of each of two photons involved in the coincidence event. In an example, before step 301, a random correction may be performed on all the coincidence events so as to remove a random coincidence event from the coincidence events. For example, the random correction may be performed with a delay method or a single photon method. Then the coincidence events may only include one or more true coincidence events and one or more scattering coincidence events, and the emission paths of each of the true coincidence events and each of the scattering coincidence events may be determined. In another example, if there are just a relatively few random coincidence events, they may be neglected without performing the random correction. Each coincidence event may include two single events, where the single event is an event in which one photon is incident on one crystal. The delay method may include: delaying a respective single event in each of the coincidence events by a period of time (such as triple the coincidence time window τ) so that delayed coincidence data may be obtained. The delayed coincidence data may be deemed to be random coincidence data. The delayed coincidence data may be removed from all coincidence data, and the rest will be true coincidence data and scattering coincidence data.

A process of the single photon method is described as follows. A cylindrical water phantom may be placed in a center of the PET device. A pharmaceutical activity in the cylindrical water phantom may ensure that a dose in the PET device is close to that in the process of scanning the subject. The cylindrical water phantom may be scanned with the scanning bed kept stationary to obtain single-photon counting rates of all crystals. With respect to crystal 1 and crystal 2 in an Line of Response $L_{12}$, the random coincidence data $D_R$ on the Line of Response $L_{12}$ may be expressed by formula (1):

$$D_R = 2 \times \tau \times S_1 \times S_2 \qquad (1).$$

Where $S_1$ represents the single photon counting rate of crystal 1 and $S_2$ represents the single photon counting rate of crystal 2. In the single photon method, the random coincidence data for each of Lines of Response may be removed.

In FIG. 1A and FIG. 1B of the present disclosure, the emission paths of a true coincidence event and a scattering coincidence event are illustrated, respectively, and the emission paths can be determined through step 301. For a coincidence event including two photons, assuming that the two photons are photon A and photon B, respectively, the two photons involved in the coincidence event may travel alone until being detected by crystals. The emission paths of the two photons may be obtained first, respectively, and the two emission paths of the two photons may have an intersecting point. Thus, the emission path of the coincidence event can be obtained according to the emission paths of the two photons involved in the coincidence event.

Figure 4:
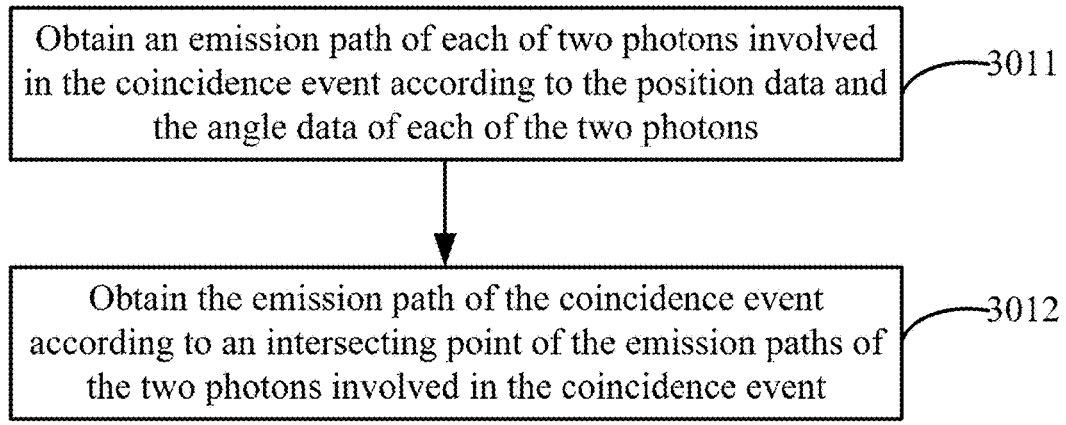
FIG. 4 is a flow diagram of a process of determining an emission path of a coincidence event according to an example of the present disclosure.

As shown in FIG. 4, the emission path of the coincidence event may be determined according to step 3011 and step 3012.

At step 3011, an emission path of each of two photons involved in the coincidence event is obtained according to the position data and the angle data of each of the two photons.

Figure 5:
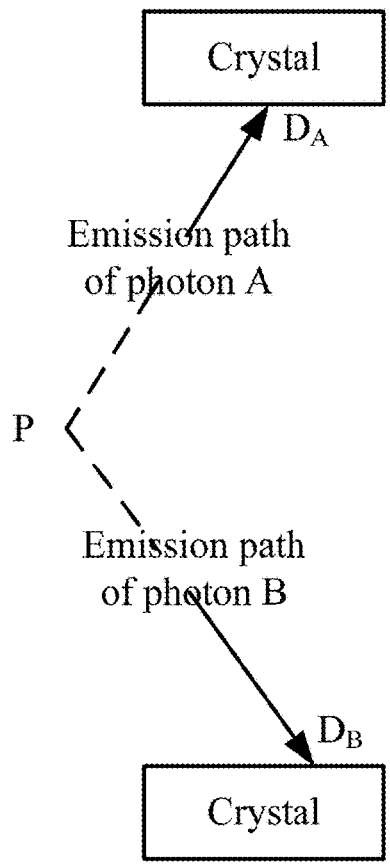
FIG. 5 is a schematic diagram of emission paths of photons in a coincidence event according to an example of the present disclosure.

In an example, assuming that the position data of the photon A is indicated as $D_A=(x_1^A, y_1^A, z_1^A)$ and its angle data, such as, the incidence vector is indicated as $\vec{V}=(l_A, m_A, n_A)$, a first linear equation of the emission path $L_A$ of the photon A may be indicated as: $x=t*l_A+x_1^A$, $y=t*m_A+y_1^A$, $z=t*n_A+z_1^A$, $t \in R$, where R represents a real number domain. The emission path of the photon A may be obtained according to the first linear equation. As shown in FIG. 5, the emission path of the photon A is the straight line $P-D_A$. In another example, assuming that the position data of the photon B is indicated as $D_B=(x_1^B, y_1^B, z_1^B)$ and its angle data is indicated as $\vec{V}=(l_B, m_B, n_B)$ a second linear equation of the emission path $L_B$ of the photon B may be indicated as: $x=t*l_B+x_1^B$, $y=t*m_B+y_1^B$, $z=t*n_B+z_1^B$, $t \in R$. The emission path of the photon B may be obtained according to the second linear equation. As shown in FIG. 5, the emission path of the photon B is the straight line $P-D_B$.

At step 3012, the emission path of the coincidence event is obtained according to an intersecting point of the emission paths of the two photons involved in the coincidence event.

For a scattering coincidence event, it can be seen that the emission paths of the photon A and the photon B will have an intersecting point according to a physical process of a positron annihilation event. Assuming that the intersecting point is indicated as $P=(x^{AB}, y^{AB}, z^{AB})$ and the emission paths of the photon A and the photon B have been determined at step 3011, an intersecting point P of the emission paths of the photon A and the photon B may be determined according to the linear equations corresponding to the two emission paths of the photon A and the photon B. Accordingly, the emission path of the coincidence event can be obtained by combining the emission paths of the photon A and the photon B at the intersecting point P. For example, $D_A P D_B$ shown in FIG. 5 is the emission path of the coincidence event.

The emission path of the coincidence event illustrated in FIG. 5 may indicate an emission path of a scattering coincidence event, which is shown in a form of a folding line. An annihilation position may be at a point (which may be not necessarily the intersecting point P) in the emission path of the coincidence event, and the photon A and the photon B produced at the annihilation position may travel along the emission path shown in FIG. 5 until being detected by crystals, respectively. Receiving positions of the photons A, B may be $D_A$ and $D_B$, respectively. For a true coincidence event, its emission path is a straight line, and two photons involved in the true coincidence event may travel in opposite directions at approximately 180 degrees until being received by crystals.

At step 302, the annihilation position of the coincidence event is determined according to the emission path of the coincidence event and the time data of each of the two photons involved in the coincidence event.

Figure 6A:
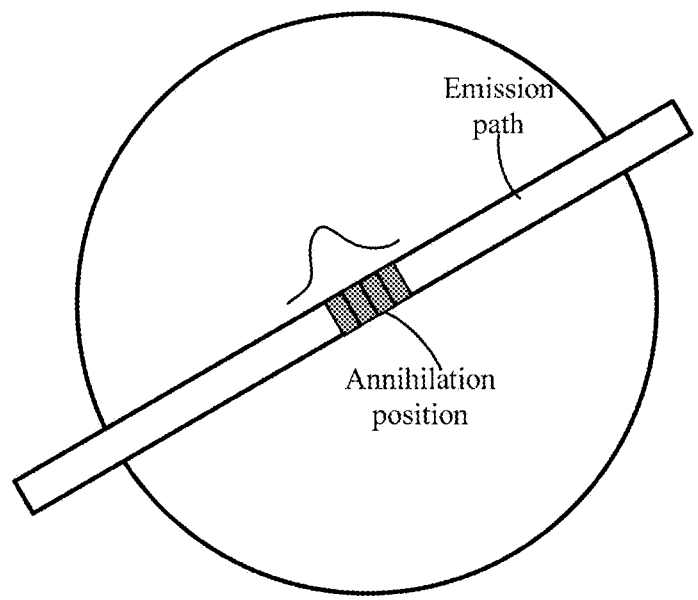
FIG. 6A is a schematic diagram of an annihilation position of a true coincidence event according to an example of the present disclosure.
Figure 6B:
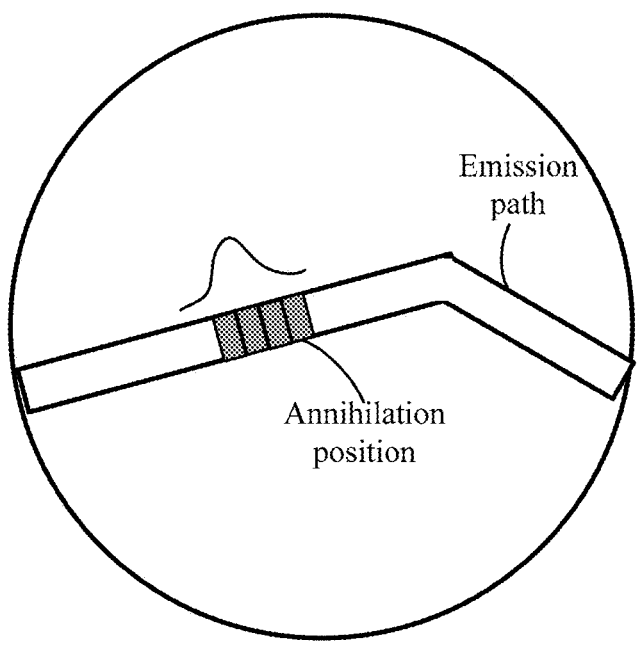
FIG. 6B is a schematic diagram of an annihilation position of a scattering coincidence event according to an example of the present disclosure.

In an example, for a true coincidence event, an approximate range where the annihilation event corresponding to the true coincidence event occurs may be estimated with the time data of the two photons involved in the annihilation event respectively arriving at crystals, as shown in FIG. 6A. For a scattering coincidence event, since the emission path of the scattering coincidence event is obtained at step 301, an approximate range where the annihilation event corresponding to the scattering coincidence event occurs in the emission path may also be estimated with the time data of the two photons involved in the scattering coincidence event, as shown in FIG. 6B.

In an example, the annihilation position may be determined according to the velocity of light and the time data of each of the two photons involved in the coincidence event. For example, a time difference $t_1-t_2$ may be obtained according to the time data $t_1$ of the photon A and the time data $t_2$ of the photon B. A difference of distances that the photon A and the photon B travel respectively may be determined according to the time difference $t_1-t_2$. Then, the annihilation position may be determined according to the distance difference and the emission path of the coincidence event. On the contrary, when an annihilation event occurs at the annihilation position shown in FIG. 6A or FIG. 6B, two photons involved in the annihilation event may travel along the emission path as shown in FIG. 6A or FIG. 6B and a time difference between the times at which the two photons are finally detected by crystals respectively may be consistent with the time difference $t_1-t_2$.

At step 303, a TOF-PET image is reconstructed according to the annihilation position, the emission path and the photon information of each of the coincidence events.

In an example, one or more model parameters of an image reconstruction model may be determined according to the annihilation position, the emission path and the photon information of each of the coincidence events, and the image reconstruction model may be constructed according to the model parameters. In an example, the image reconstruction model may be expressed by formula (2):

$$Y_j = P_{ij} X_i A_j N_j + R_j \quad (2).$$

In the above formula (2), j may represent an emission path of a coincidence event which may include a straight line path of a true coincidence event or a folding line path of a scattering coincidence event; $Y_j$ may represent all coincidence data on the emission path j; $X_i$ may represent an i-th voxel in a PET image indicated by the annihilation position; $P_{ij}$ may represent a probability that the i-th voxel is received by the emission path j; $A_j$ may represent an attenuation probability on the emission path j, where the attenuation probability may be different with respect to the respective emission paths; $N_j$ may represent a normalization factor on the emission path j, where the factor may be determined in conjunction with the annihilation position; and $R_j$ may represent random coincidence data on the emission path j.

It is noted that $P_{ij}$ is a multivariable function, and for each of i, $P_{ij}$ is associated with the structure of two corresponding detectors, the i-th voxel, two crystals involved in the i-th voxel, the angle data of the two crystals involved in the i-th voxel, and the time data of the two crystals involved in the i-th voxel. $A_j$ can be determined based on an emission path of a coincidence event. $N_j$ can be also determined based on the emission path of a coincidence event. $P_{ij}$, $A_j$ and $N_j$ may be determined with a conventional method, which will not be redundantly described herein.

An iterative reconstruction formula may be obtained according to the image reconstruction model. In an example, the iterative reconstruction formula may be expressed by formula (3):

$$x^{(k+1)} = \frac{1}{\sum_j p_{ij}} x^{(k)} \sum_{evt} \frac{p_{ij}}{A_j N_j \sum_{i'} p_{i'j} x_{i'}^{(k)} + R_j}, \quad (3)$$

where evt represents all coincidence data, k represents a number of iterations, and i' represents i'-th voxel, which is independent from i. A TOF-PET image may be reconstructed according to the iterative reconstruction formula (3).

The method of reconstructing a PET image in the present disclosure, both true coincidence data and scattering coincidence data contribute to reconstructing the PET image, and therefore, the utilization rate of the collected data can be increased. Further, an actual emission path of a scattering coincidence event may be determined with the method, without performing scattering correction when reconstructing the PET image, thereby reducing the amount of calculation and improving the efficiency of PET image reconstruction.

Figure 7:
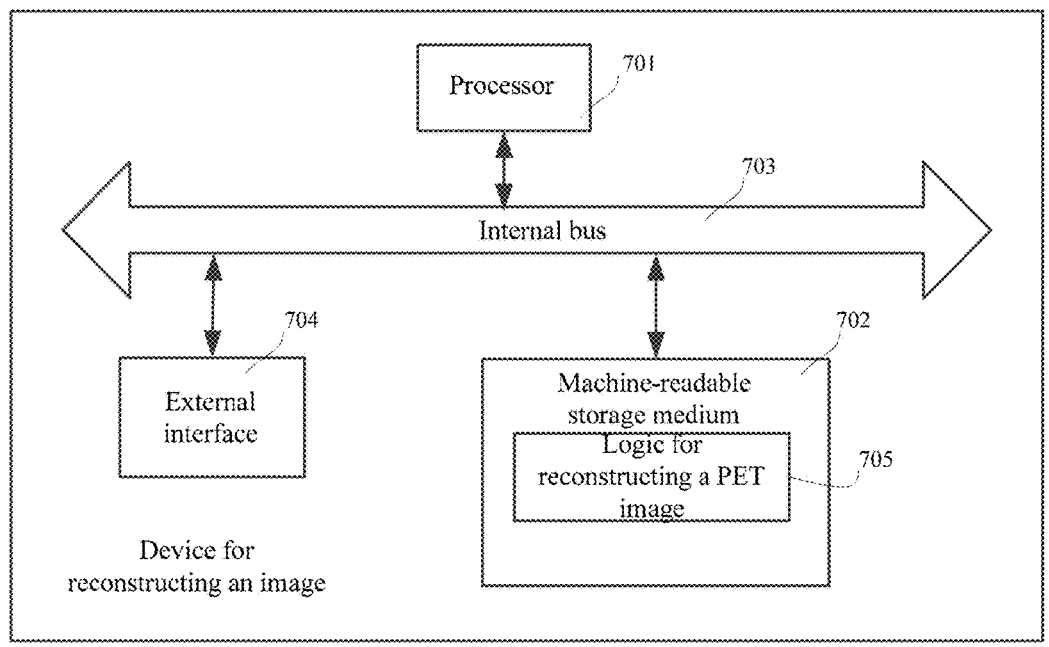
FIG. 7 is a schematic diagram of a hardware structure of a device for reconstructing an image according to an example of the present disclosure.

As shown in FIG. 7, corresponding to the above method, the present disclosure further provides a device for reconstructing an image. In a TOF-PET device, after detecting a γ-photon produced by an annihilation event, a detector may obtain the photon information such as time data, position data and angle data of the γ-photon, and perform coincidence determination according to the above photon information to determine a coincidence event. The photon information of the coincidence event may be transmitted to the device for reconstructing an image, so that the device for reconstructing an image can reconstruct a PET image according to the photon information of the coincidence event.

Figure 8:
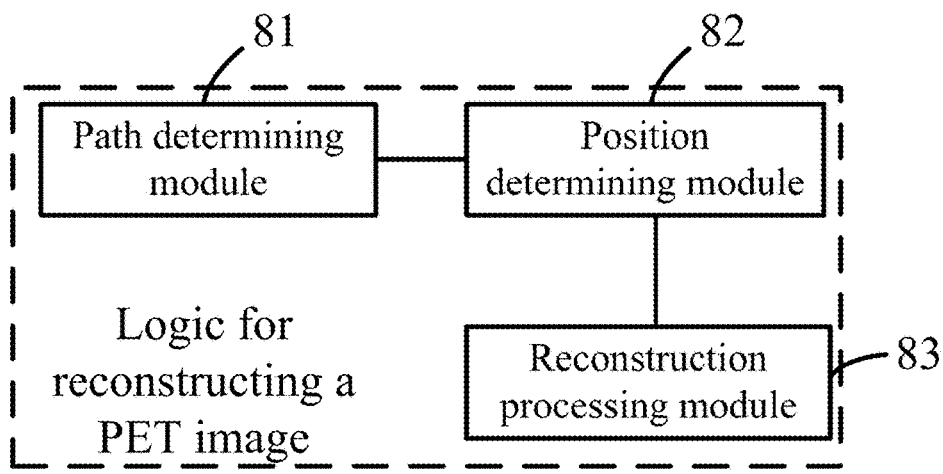
FIG. 8 is a schematic module diagram of logic for reconstructing an image according to an example of the present disclosure.

As shown in FIG. 7, the device may include a processor 701 and a machine-readable storage medium 702, where the processor 701 and the machine-readable storage medium 702 can be interconnected by an internal bus 703. The device may further include an external interface 704 so that it can communicate with other devices or members. Further, instructions corresponding to logic 705 for reconstructing a PET image may be stored on the machine-readable storage medium 702. As shown in FIG. 8, the logic 705 may include a plurality of logic modules divided by functions.

As shown in FIG. 8, the logic for reconstructing a PET image may be used to reconstruct a PET image according to photon information of coincidence events. From a functional point of view, the logic may include a path determining module 81, a position determining module 82 and a reconstruction processing module 83.

The path determining module 81 may be configured to for each of coincidence events including at least one true coincidence event and at least one scattering coincidence event, determine an emission path of the coincidence event according to photon information of the coincidence event, where the photon information of the coincidence event includes time data, position data, and angle data of each of two photons involved in the coincidence event.

The position determining module 82 may be configured to determine an annihilation position of the coincidence event according to the emission path of the coincidence event and the time data of each of the two photons involved in the coincidence event.

The reconstruction processing module 83 may be configured to reconstruct a TOF-PET image according to the annihilation position, the emission path and the photon information of each of the coincidence events.

In an example, the path determining module 81 may be configured to respectively obtain an emission path of each of the two photons involved in the coincidence event according to the position data and the angle data of each of the two photons, and determine an intersecting point of the emission paths of the two photons to obtain the emission path of the coincidence event.

In an example, the path determining module 81 may further be configured to, for each of the photons involved in the coincidence events, obtain respective incidence intersecting positions on at least two crystal layers of a crystal array which indicate a travelling trace of the photon incident into the crystal array, and obtain the angle data of the photon incident into the crystal array according to the respective incidence intersecting positions.

In an example, the position data of the photon indicates an incidence intersecting position of the photon on the crystal layer at which the photon arrives finally.

Figure 9:
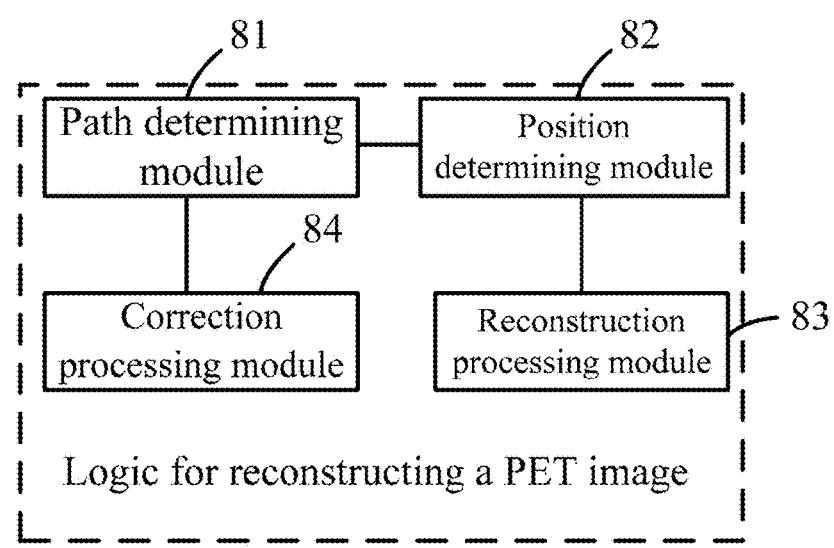
FIG. 9 is a schematic module diagram of logic for reconstructing an image according to another example of the present disclosure.

In an example, as shown in FIG. 9, the logic 705 may further include a correction processing module 84 configured to perform a random correction to remove a random coincidence event from the coincidence events before determining the respective emission paths of the coincidence events.

In an example, the reconstruction processing module 83 may be configured to determine one or more model parameters of an image reconstruction model according to the annihilation position, the emission path and the photon information of each of the coincidence events; construct the image reconstruction model according to the model parameters; derive an iterative reconstruction formula from the image reconstruction model; and reconstruct the PET image with the iterative reconstruction formula.

In different examples, the machine readable storage medium 702 may be: a Read-Only Memory (ROM), a volatile memory, a non-volatile memory, a flash memory, a storage drive (e.g. hard disk drive), a solid state hard disk, any type of storage disk (e.g., optical disk, Digital Video Disk (DVD)), or a similar storage medium, or a combination thereof.

Taking software implementation as an example, it is further described that how the device for reconstructing an image runs the logic for reconstructing an image. In this example, the logic for reconstructing an image in the present disclosure should be understood as machine-executable instructions stored on the machine-readable storage medium 702. When the processor 701 on the device for reconstructing an image in the present disclosure executes the logic, the processor 701 may be caused to execute the above method of reconstructing a PET image by invoking the machine-executable instructions corresponding to the logic stored on the machine-readable storage medium 702.

For simplicity and illustrative purposes, the present disclosure is described by referring mainly to examples thereof. In the above descriptions, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

The above description merely provides examples of the present disclosure and is not intended to limit the present disclosure in any form. Although the present disclosure is disclosed by the above examples, the examples are not intended to limit the present disclosure. Those skilled in the art, without departing from the scope of the technical scheme of the present disclosure, may make a plurality of changes and modifications of the technical scheme of the present disclosure by the method and technical content disclosed above.

Therefore, without departing from the scope of the technical scheme of the present disclosure, based on technical essences of the present disclosure, any simple alterations, equal changes and modifications should fall within the protection scope of the technical scheme of the present disclosure. Accordingly, other examples are within the scope of the following claims.

The invention claimed is:

1. A method of reconstructing a Positron Emission Computed Tomography (PET) image, the method comprising:
for each of coincidence events comprising at least one true coincidence event and at least one scattering coincidence event,
determining an emission path of the coincidence event according to photon information of the coincidence event, wherein the photon information of the coincidence event comprises time data, position data, and angle data of each of two photons involved in the coincidence event;
determining an annihilation position of the coincidence event according to the emission path of the coincidence event and the time data of each of the two photons involved in the coincidence event; and
reconstructing the PET image according to the annihilation position, the emission path and the photon information of each of the coincidence events.

2. The method of claim 1, wherein determining the emission path of the coincidence event comprises:
for each of the two photons involved in the coincidence event, obtaining a respective emission path according to the position data and the angle data of the photon; and
determining an intersecting point of the respective emission paths of the two photons to obtain the emission path of the coincidence event.

3. The method of claim 2, further comprising:
for each of the photons involved in the coincidence event, obtaining respective incidence intersecting positions on at least two crystal layers of a crystal array, the incidence intersecting positions indicating a travelling trace of the photon incident into the crystal array; and
obtaining the angle data of the photon incident into the crystal array according to the respective incidence intersecting positions.

4. The method of claim 3, wherein the position data of the photon includes an incidence intersecting position of the photon on a crystal layer at which the photon arrives finally in the crystal array.

5. The method of claim 1, wherein determining the annihilation position of the coincidence event comprises:

obtaining a difference of traveling time of the two photons before detected according to the time data of each of the two photons involved in the coincidence event;
determining a difference of traveling distance of the two photons along the emission path according to a velocity of light and the traveling time difference; and
determining the annihilation position in the emission path according to the traveling distance difference and the emission path.

6. The method of claim 1, further comprising:
performing a random correction to remove a random coincidence event from the coincidence events before determining the respective emission paths of the coincidence events.

7. The method of claim 6, wherein performing the random correction comprises:
delaying a respective single event in each of the coincidence events by a period of time to obtain delayed coincidence data, a length of the period of time being larger than a coincidence time window; and
removing the delayed coincidence data from coincidence data of the coincidence events.

8. The method of claim 6, wherein performing the random correction comprises:
for each of the coincidence events, obtaining a Line of Response associated with the determined emission path;
obtaining respective single photon counting rates of two crystals associated with the Line of Response;
determining random coincidence data for the Line of Response according to the single photon counting rates of the two crystals and a coincidence time window; and
removing the random coincidence data for the Line of Response from coincidence data of the coincidence events.

9. The method of claim 1, wherein reconstructing the PET image according to the annihilation position, the emission path and the photon information of each of the coincidence events comprises:
determining one or more model parameters of an image reconstruction model according to the annihilation position, the emission path and the photon information of each of the coincidence events;
constructing the image reconstruction model according to the model parameters;
deriving an iterative reconstruction formula from the image reconstruction model; and
reconstructing the PET image with the iterative reconstruction formula.

10. The method of claim 9, wherein the image reconstruction model is expressed as:

$$Y_j = P_{ij} X_i A_j N_j + R_j,$$

wherein j represents an emission path of the coincidence event,
$Y_j$ represents coincidence data of the coincidence event on the emission path j,
$X_i$ represents an i-th voxel in the PET image,
$P_{ij}$ represents a probability that the i-th voxel is received by the emission path j,
$A_j$ represents an attenuation probability on the emission path j,
$N_j$ represents a normalization factor on the emission path j, and
$R_j$ represents random coincidence data on the emission path j, and wherein determining the one or more model parameters of
the image reconstruction model comprises:
obtaining j from the determined emission paths of the
coincident events,
determining $A_j$ and $N_j$ based on the emission path j,
determining $X_i$ based on the annihilation position, and
determining $P_{ij}$ based on the angle data and the time
data of two crystals involved in the i-th voxel and the
emission path j.

11. A device for reconstructing a PET image, the device comprising:
a processor; and
a machine-readable storage medium to store machine-executable instructions corresponding to logic for reconstructing a PET image,
by reading and executing the machine-executable instructions, the processor is caused to:
for each of coincidence events comprising at least one true coincidence event and at least one scattering coincidence event,
determine an emission path of the coincidence event according to photon information of the coincidence event, wherein the photon information of the coincidence event comprises time data, position data, and angle data of each of two photons involved in the coincidence event;
determine an annihilation position of the coincidence event according to the emission path of the coincidence event and the time data of each of the two photons involved in the coincidence event; and
reconstruct the PET image according to the annihilation position, the emission path and the photon information of each of the coincidence events.

12. The device of claim 11, wherein, for determining the emission path of the coincidence event, the machine-executable instructions cause the processor to:
for each of the two photons involved in the coincidence event, obtain a respective emission path according to the position data and the angle data of the photon; and
determine an intersecting point of the respective emission paths of the two photons to obtain the emission path of the coincidence event.

13. The device of claim 12, wherein the machine-executable instructions further cause the processor to:
for each of the photons involved in the coincidence event, obtain respective incidence intersecting positions on at least two crystal layers of a crystal array, the incidence intersecting positions indicating a travelling trace of the photon incident into the crystal array; and
obtain the angle data of the photon incident into the crystal array according to the respective incidence intersecting positions.

14. The device of claim 13, wherein the position data of the photon includes an incidence intersecting position of the photon on a crystal layer at which the photon arrives finally in the crystal array.

15. The device of claim 11, wherein for determining the annihilation position of the coincidence event, the machine-executable instructions cause the processor to:
obtain a difference of traveling time of the two photons before detected according to the time data of each of the two photons involved in the coincidence event;
determine a difference of traveling distance of the two photons along the emission path according to a velocity of light and the traveling time difference; and
determine the annihilation position in the emission path according to the traveling distance difference and the emission path.

16. The device of claim 11, wherein the machine-executable instructions further cause the processor to:
perform a random correction to remove a random coincidence event from the coincidence events before determining the respective emission paths of the coincidence events.

17. The device of claim 16, wherein for performing the random correction, the machine-executable instructions cause the processor to:
delay a respective single event in each of the coincidence events by a period of time to obtain delayed coincidence data, a length of the period of time being larger than a coincidence time window; and
remove the delayed coincidence data from coincidence data of the coincidence events.

18. The device of claim 16, wherein for performing the random correction, the machine-executable instructions cause the processor to:
for each of the coincidence events, obtain a Line of Response associated with the determined emission path;
obtain respective single photon counting rates of two crystals associated with the Line of Response;
determine random coincidence data for the Line of Response according to the single photon counting rates of the two crystals and a coincidence time window; and
remove the random coincidence data for the Line of Response from coincidence data of the coincidence events.

19. The device of claim 11, wherein for reconstructing the PET image according to the annihilation position, the emission path and the photon information of each of the coincidence events, the machine-executable instructions cause the processor to:
determine one or more model parameters of an image reconstruction model according to the annihilation position, the emission path and the photon information of each of the coincidence events;
construct the image reconstruction model according to the model parameters;
deriving an iterative reconstruction formula from the image reconstruction model; and
reconstruct a PET image with the iterative reconstruction formula.

20. A non-transitory machine-readable storage medium having machine-executable instructions stored thereon which, when executed by one or more processors, cause the one or more processors to perform operations for reconstructing a PET image, the operations comprising:
for each of coincidence events comprising at least one true coincidence event and at least one scattering coincidence event,
determining an emission path of the coincidence event according to photon information of the coincidence event, wherein the photon information of the coincidence event comprises time data, position data, and angle data of each of two photons involved in the coincidence event;
determining an annihilation position of the coincidence event according to the emission path of the coincidence event and the time data of each of the two photons involved in the coincidence event; and reconstructing the PET image according to the annihilation position, the emission path and the photon information of each of the coincidence events.

* * * * *